United States Patent [19]

Green et al.

[11] Patent Number: 4,917,114

[45] Date of Patent: Apr. 17, 1990

[54] SURGICAL FASTENER AND SURGICAL STAPLING APPARATUS

[75] Inventors: David T. Green, Norwalk; Herbert W. Korthoff, Wilton, both of Conn.

[73] Assignee: United States Surgical Corporation, Norwalk, Conn.

[21] Appl. No.: 176,695

[22] Filed: Apr. 1, 1988

Related U.S. Application Data

[62] Division of Ser. No. 920,581, Oct. 17, 1986, Pat. No. 4,752,024.

[51] Int. Cl.⁴ .................. A61B 17/04; A61B 17/08; A61B 19/00; A41F 1/00
[52] U.S. Cl. .................... 227/179; 24/616; 411/509; 411/457; 411/512
[58] Field of Search ............ 128/334 R, 334 C, 335, 128/337, 354, 346; 227/DIG. 1; 24/615, 616, 590, 598, 621, 297, 295; 411/509, 457, 512, 432, 433, 908, 918

[56] References Cited

U.S. PATENT DOCUMENTS

| | | | |
|---|---|---|---|
| 833,458 | 10/1906 | Hausherr | 24/615 |
| 874,957 | 12/1907 | Godley | 24/615 |
| 1,480,746 | 1/1924 | DeBie | 411/457 |
| 3,258,012 | 6/1966 | Nakayama et al. | 128/334 C |
| 4,233,981 | 11/1980 | Schomacher | 128/334 R |
| 4,351,466 | 9/1982 | Nolies | 128/334 R |
| 4,356,601 | 11/1982 | Kimura | 24/297 |
| 4,473,077 | 9/1984 | Nolies et al. | 128/334 R |
| 4,488,523 | 12/1984 | Shichman | 128/334 R |
| 4,508,374 | 4/1985 | Kantor | 285/319 |
| 4,534,088 | 8/1985 | Ricke | 24/297 |
| 4,624,257 | 11/1986 | Berggren et al. | 128/334 C |
| 4,632,435 | 12/1986 | Polyak | 285/331 |
| 4,666,355 | 5/1987 | Stover | 411/432 |
| 4,747,407 | 5/1988 | Liu et al. | 128/334 C |
| 4,780,037 | 10/1988 | Payne | 411/512 |

FOREIGN PATENT DOCUMENTS

1103760  6/1955  France .................. 411/509

Primary Examiner—Edward M. Coven
Assistant Examiner—Gary Jackson
Attorney, Agent, or Firm—Kenyon & Kenyon

[57] ABSTRACT

The two-part surgical fastener is composed of an annular stapling part having projecting prongs and annular retaining board having an annular gap which receives the prongs. Barbs on the prongs serve to abut against a retaining ring on the retaining part to maintain a fixed relationship between the parts for stapling purposes. The anvil assembly on which the retaining part of the fastener is mounted as fingers which can be collapsed radially inwardly after stapling to permit ease of removal.

12 Claims, 9 Drawing Sheets

SURGICAL FASTENER AND SURGICAL STAPLING APPARATUS

This is a division of application Ser. No. 920,581 filed Oct. 17, 1986, now U.S. Pat. No. 4,752,024.

This invention relates to a surgical fastener and to a surgical stapling apparatus.

Heretofore, various types of surgical stapling devices have been known wherein a stapling function takes place at a location which is relatively remote for the location at which the stapling device is held and actuated by an operator. For example linear closure surgical stapler devices are described in U.S. Pat. No. 3,494,533 and circular anastomosis surgical stapler devices are described in U.S. Pat. Nos. 4,304,236; 4,351,466; 4,473,077 and 4,488,523 as well as U.S. Pat. Nos. D. 273,041 and 271,944. Typically, the stapling devices described in these patents operate by placing tissue to be stapled in a clamped manner between an anvil assembly and a fastener holding assembly, both of which are located at the distal end of the instrument The clamped tissue is stapled by driving one or more fasteners from the holding assembly so that the ends of the fasteners pass through the tissue and are formed properly by contact with the anvil assembly. The forces required to operate the instrument are applied by the operator of the instrument to one or more actuator elements located at or near the proximal end of the instrument. The distal and proximal portions of the instrument are joined by a longitudinal connecting shaft structure along which the actuating forces and motions are transmitted to the distal operation elements. This type of construction, including relatively widely spaced distal and proximal portions, may be employed for any of several reasons, such as the relative inaccessibility of the tissue to be stapled, the need for good visibility of the tissue during stapling, and the like.

These known types of surgical stapler devices generally use a plurality of small and discrete fasteners requiring precise registration with the anvil assembly to ensure that proper fastener formation occurs during the stapling operation.

Accordingly, it is an object of the invention to provide a unitary surgical fastener having a multiplicity of fastening points.

It is another object of the invention to eliminate the need for a plurality of precisely registered small and discrete fasteners in anastomosis stapling devices.

It is another object of the invention to provide a surgical stapler which can be easily and quickly installed in tissue by a surgical stapling apparatus.

It is another object of the invention to eliminate the need for a high degree of rotational accuracy in the registration of a fastener holder relative to an anvil assembly in an anastomosis stapling device.

Briefly, the invention provides a surgical fastener which is comprised of an annular stapling part having a plurality of axially extending circumferentially spaced prongs each of which has a sharp tip for piercing tissue. In addition, the fastener has an annular retaining part with an annular gap for receiving the prongs of the stapling part. In addition, catch means are provided for holding the prongs in the retaining part in order to clamp pierced tissue therebetween. For example, the catch means may include a radially extending barb on at least one of the prongs for abutting against the retaining part The retaining ring may also include a cylindrical guide wall about the retaining ring in order to define an annular gap to receive the prongs of the stapling part. Suitable means are also provided for securing the guide wall to the retaining ring.

The invention also provides a method of stapling the tubular ends of a pair of vessels together which includes the steps of clamping the tubular ends of the vessels between an anvil assembly and a surgical fastener holding assembly, driving an annular stapling part through the clamped ends of the tissue into an annular retaining part removably supported on the anvil assembly and severing the clamped ends on a circular cutting line disposed radially within the stapling part.

These and other objects and advantages of the invention will become more apparent from the following detailed description taken in conjunction with the accompanying drawings wherein.

Figure 1:
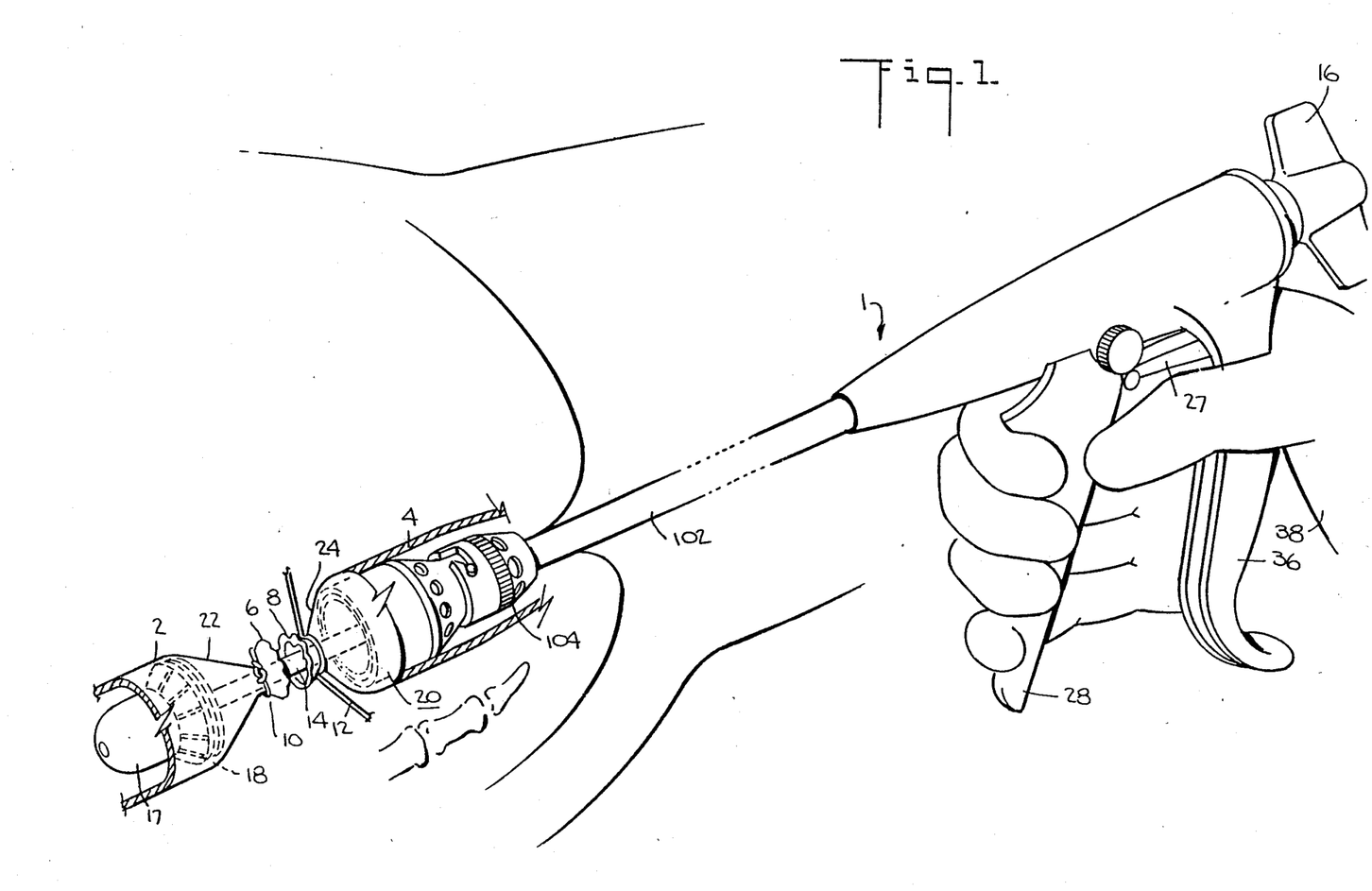
FIG. 1 illustrates a perspective view of a surgical stapling apparatus constructed in accordance with the invention in place within an intestine.
Figures 4, 5:
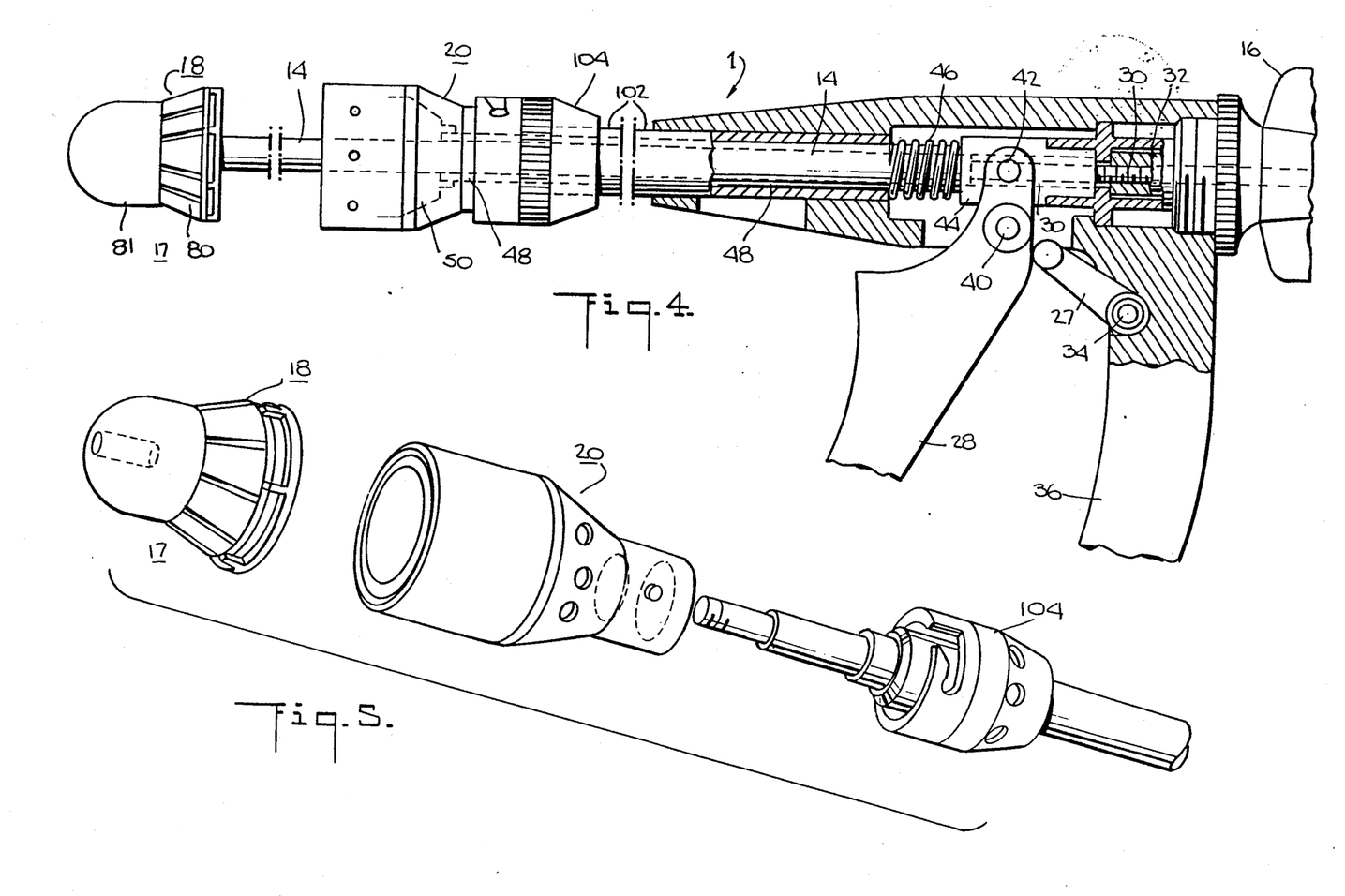
FIG. 4 illustrates a part sectional side view of the apparatus of FIG. 1.
FIG. 5 illustrates an exploded view of the distal end of the apparatus of FIG. 1.

Referring to FIGS. 1 and 4, the surgical stapling apparatus 1 is used, for example for the stapling of two ends 2, 4 of an intestine wherein a section of the intestine has been surgically removed between cut ends 6, 8. As indicated in FIG. 1, the cut ends 6, 8 of the intestine are generally tied with suture material 10, 12 with conventional purse-string suturing being used.

The stapling apparatus 1 includes a shaft 14 and a hand screw 16 which is articulated to the shaft 14 in order to move the shaft 14. As indicated in FIG. 4, the apparatus 1 includes an anvil assembly 17 which is mounted on a distal end of the shaft 14 and includes an anvil 18 which faces a surgical fastener holding assembly 20 which is also mounted on the shaft 14 for relative movement with the anvil assembly 17 to maintain the two ends of the intestine areas 22, 24 therebetween (see FIG. 1).

Referring to FIG. 4, the shaft 14 is provided with a screwthread 30 at the proximal end which mates in an internally threaded sleeve extension 32 of the hand screw 16. The sleeve extension 32 is secured to the hand screw 16 so that both turn together and thus the rotation of the hand screw 16 causes longitudinal movement of the shaft 14. By tightening the hand screw 16, the anvil assembly 17 can be moved towards the holding assembly 20 so that the tissue can be clamped therebetween with proper spacing between the anvil assembly 17 and the holding assembly 20. Calibration means (not shown) may be provided to ensure proper spacing, for example as described in U.S. Pat. No. 4,473,077.

The apparatus 1 is also provided with a handle 36 and a trigger 28 which is pivotally mounted on a pivot pin 40 secured in the housing of the apparatus 1. A safety latch 27 is also pivotally mounted on a pivot pin 34 on the handle 36 in order to prevent pivoting of the trigger 28. In addition, the trigger 28 is articulated in known manner, for example via a pusher 42 to a slider 44 disposed about the shaft 14. This slider 44 abuts a compression spring 46 in order to apply a biasing force on a tube 48 concentric of the sleeve 14 in order to move the tube 48 distally upon actuation of the trigger 28. The tube 48, in turn, cooperates with an actuator 50 in order to perform a stapling operation.

Referring to FIGS. 4 and 5, the shaft 14 has a threaded distal end on which the anvil assembly 17 is mounted in threaded manner. In addition, a bayonet mount 104 is secured, in known manner on the tube 48. In this regard, the holding assembly 20 includes a sleeve at the proximal end which carries a pin for fitting into the bayonet connection of the mount 104. As indicated in FIG. 4, a sheath 102 is provided over the central part of the instrument and has a tubular portion 53 fitting within the bayonet mount 104 (see FIG. 12).

Figures 2, 3:
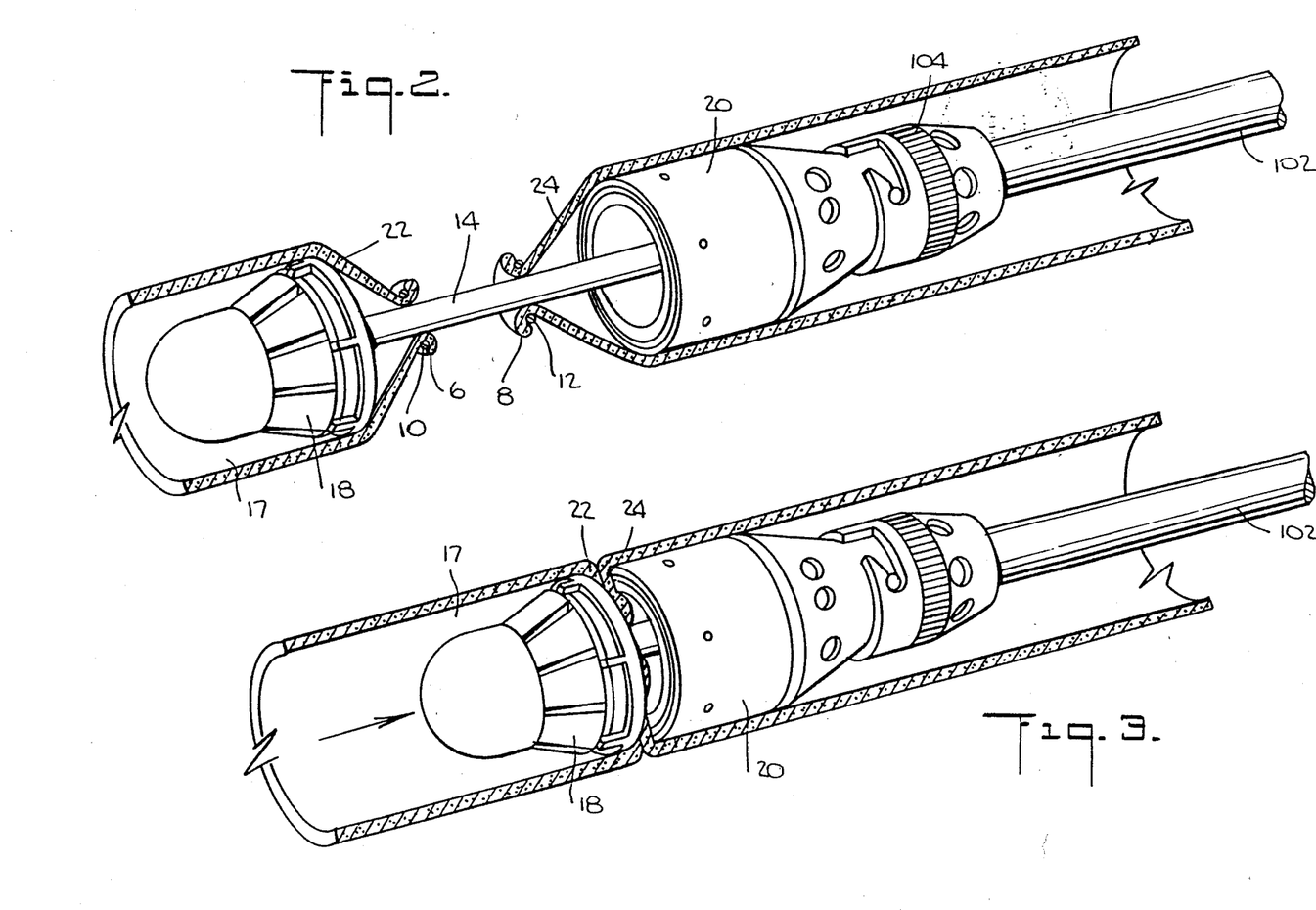
FIG. 2 illustrates a perspective view of the distal end of the stapling apparatus prior to fastening.
FIG. 3 illustrates a view similar to FIG. 2 of the distal end of the stapling apparatus during a stapling operation.

Referring to FIGS. 2 and 3, when the apparatus is initially put in place, the cut ends 6, 8 of the body tissue are drawn in about the shaft 14 with the anvil assembly 17 in a spaced condition relative to the holding assembly 20. During stapling, the anvil assembly 17 is drawn against the holding assembly 20 so as to clamp the ends of the tissue between the anvil assembly 17 and the holding assembly 20 (see FIG. 3).

Figures 6, 7, 8:
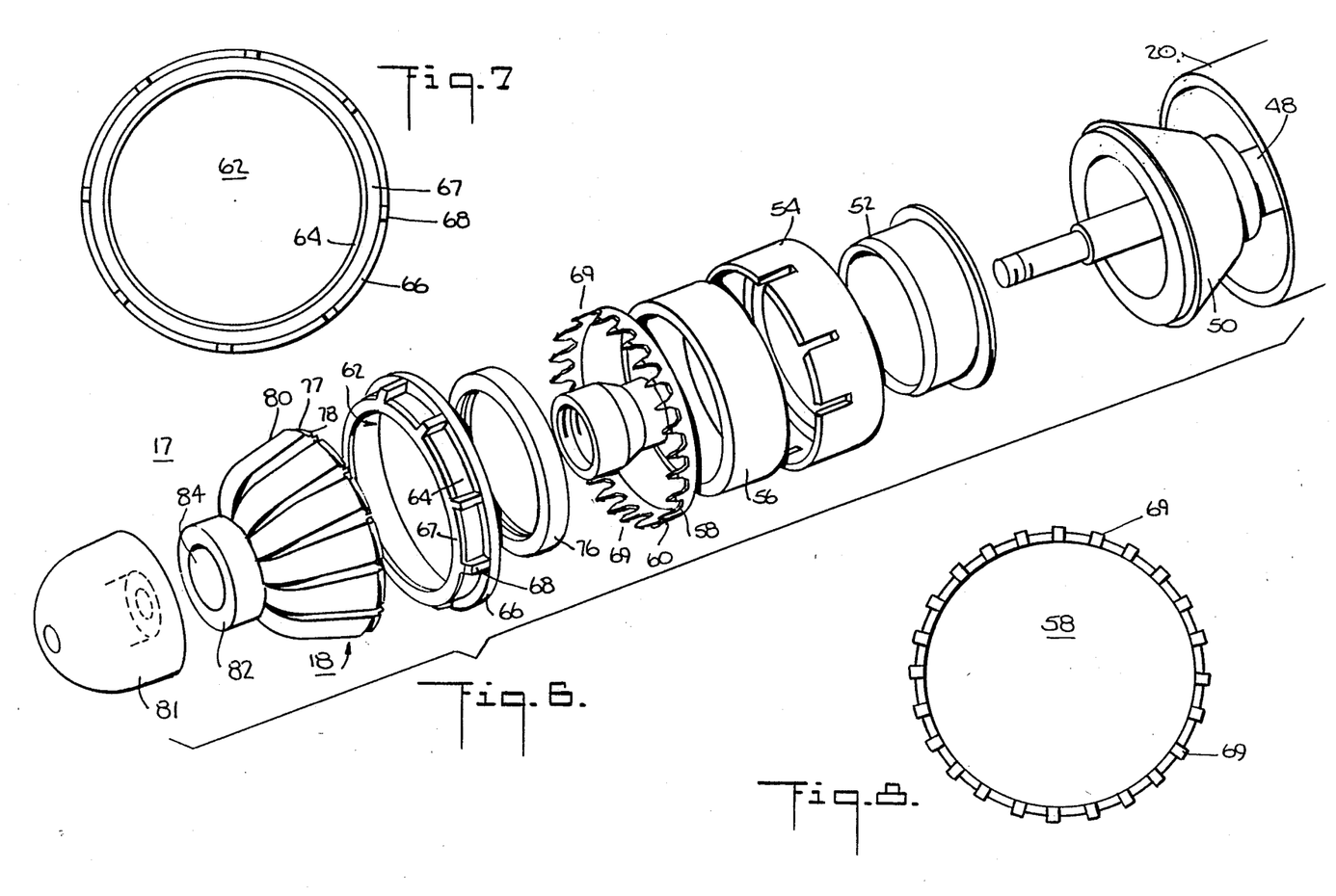
FIG. 6 illustrates an exploded view of a surgical fastener, anvil assembly and holding assembly in accordance with the invention.
FIG. 7 illustrates a front view of an annular retaining part in accordance with the invention.
FIG. 8 illustrates a front view of an annular stapling part in accordance with the invention.
Figure 12:
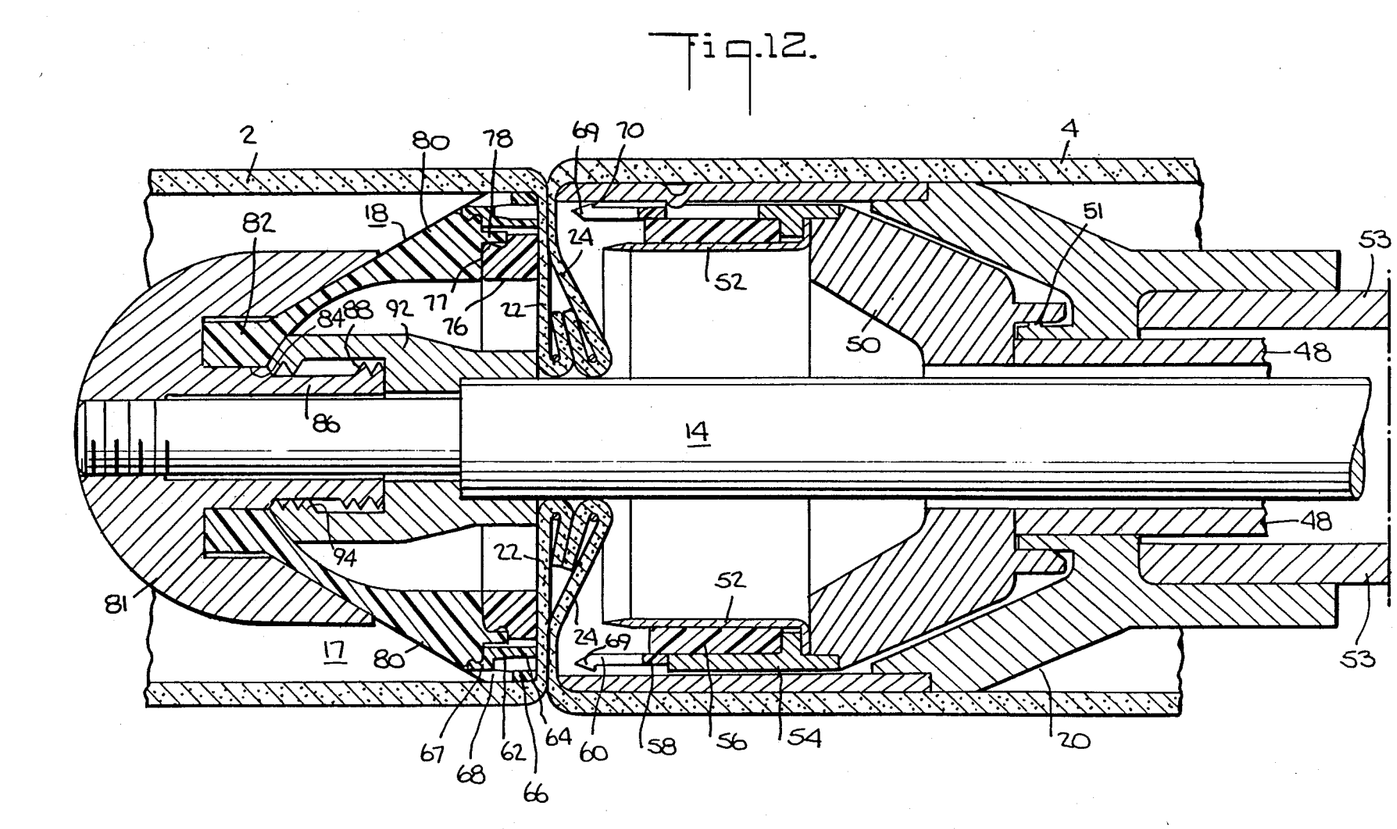
FIG. 12 illustrates a cross sectional view of the stapling components of the apparatus during an initial phase of stapling.

Referring to FIGS. 6 and 12, the actuator means includes an actuator 50 which is abutted against the distal end of the tube 48 and is disposed within the holding assembly 20. In this respect, the holding assembly is provided with a pad 51 (FIG. 12) which frictionally retains the actuator 50 in place until the actuator 50 is driven clear of the pad 51 by the tube 48. The actuator 50 carries an annular push ring 54 as well as an annular blade or scalpel 52 which is retained between the actuator 50 and push ring 54. In addition, a plastic spacer ring 56 is concentrically disposed between the push ring 54 and the annular scalpel 52. As indicated in FIG. 6, the push ring 54 is provided with a plurality of circumferentially disposed slots at the distal end.

An annular stapling part 58 is mounted about the spacer ring 56 and against the push ring 54 (see FIG. 12) and has a plurality of axially extending circumferentially spaced prongs 60.

The anvil 18 is made of resilient material and has a plurality of radiating fingers 80 extending angularly outwardly from a central hub 82 concentrically disposed about the longitudinal axis of the shaft 14. In this regard, the anvil 18 is made of one piece with several fingers 80. As indicated in FIG. 6, the anvil 18 has a somewhat frustum-like shape with the cylindrical hub 82 at the distal end. In addition, each finger 80 tapers in both thickness and width from the free end to the hub 82. In addition, the free end of each finger 80 has an extension 78 which forms a basal ridge as well as an annular reaction surface 77 within the extension 78.

An annular cutting block 76 is removably mounted within the outer ends of the fingers 80. That is, the cutting block 76 abuts against the reaction surfaces 77 of the fingers 80 within the extension 78. As indicated in FIG. 12, the cutting block 76 is aligned with the annular scalpel 52 and is made of a material so as to be penetrated by the cutting edge of the scalpel 52. The cutting block 76 is also shaped so as to be fitted into and about the extensions 78 in a slide fit manner.

An annular retaining part 62 is also mounted at the free ends of the fingers 80 of the anvil 18. As indicated, the retaining part 62 includes an inner cylindrical guide wall 64 and an outer retaining ring 66 which are concentrically disposed relative to each other to define an annular gap for receiving the prongs 60. To this end, the gap is of an axial length less than an axial length of the prongs 60 to permit passage of the prongs 60 therethrough. Suitable means in the form of posts 68 (FIG. 8) are provided to secure the retaining ring 66 to the cylindrical wall 64. An annular flange 67 is also provided between the post 68 and the guide wall 64 (FIG. 7).

Figure 9:
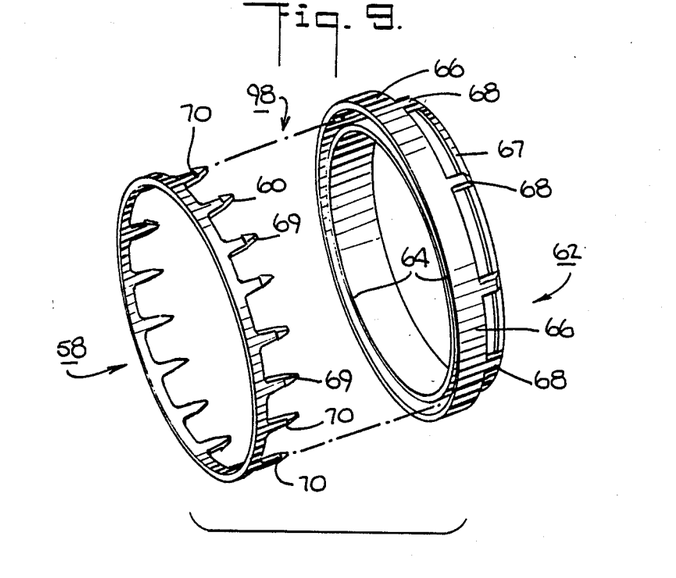
FIG. 9 illustrates an exploded view of the retaining part and stapling part in accordance with the invention.
Figure 10:
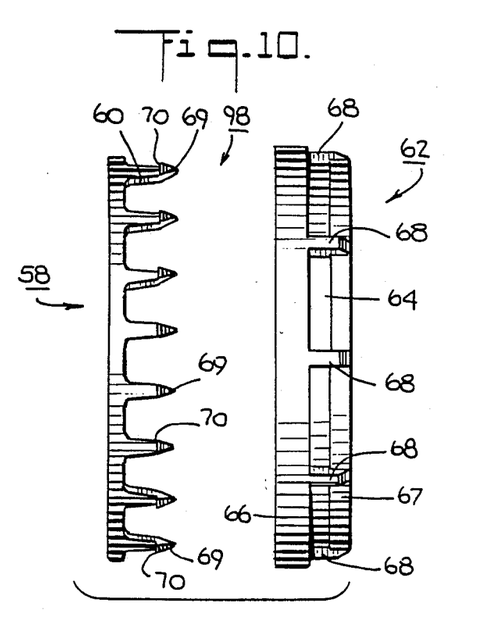
FIG. 10 illustrates side views of the retaining part and stapling part of FIG. 9.

Referring to FIGS. 9 and 10, wherein like reference characters indicate like parts as above, each prong 60 of the stapling part 58 has a sharp tip for piercing tissue while the retaining part 62 is positioned to receive the prongs 60. Catch means are also provided for holding the prongs 60 in the retaining part 62 in order to clamp the pierced tissue therebetween. As illustrated, the catch means includes a radially extending barb 69 on each prong 60 with a proximally facing surface 70 which can be engaged against the retaining ring 66 of the retaining part 62. As indicated, each barb 69 extends radially outwardly of a prong 60 so that the proximally facing surface 70 can be engaged against the retaining ring 66 and particularly on a side remote from the stapling part 58.

The annular stapling part 58 and annular retaining part 62 form a surgical fastening 98 which is of relatively simple construction. Both parts 58, 62 can be rotated relative to the other and need not be precisely registered in order to provide for stapling.

When the two parts 58, 62 are brought together, the prongs 60 pierce the tissue and then enter into the gap between the guide walls 64 and retaining ring 66. At this time, the guide wall 64 and ring 66 temporarily deform due to the wedging action of the barbs 69. After the barbs 69 clear the retaining ring 66, the ring 66 and wall 64 snap back into their normal relationship in which the surfaces 70 of the barbs 69 engage against the retaining ring 66 thus securing the parts 58, 62 together while also clamping the two ends of tissue together. Of note, the flange 67 protects uninvolved tissue from the sharp ends of the prongs 60 (see FIG. 13).

Figure 11:
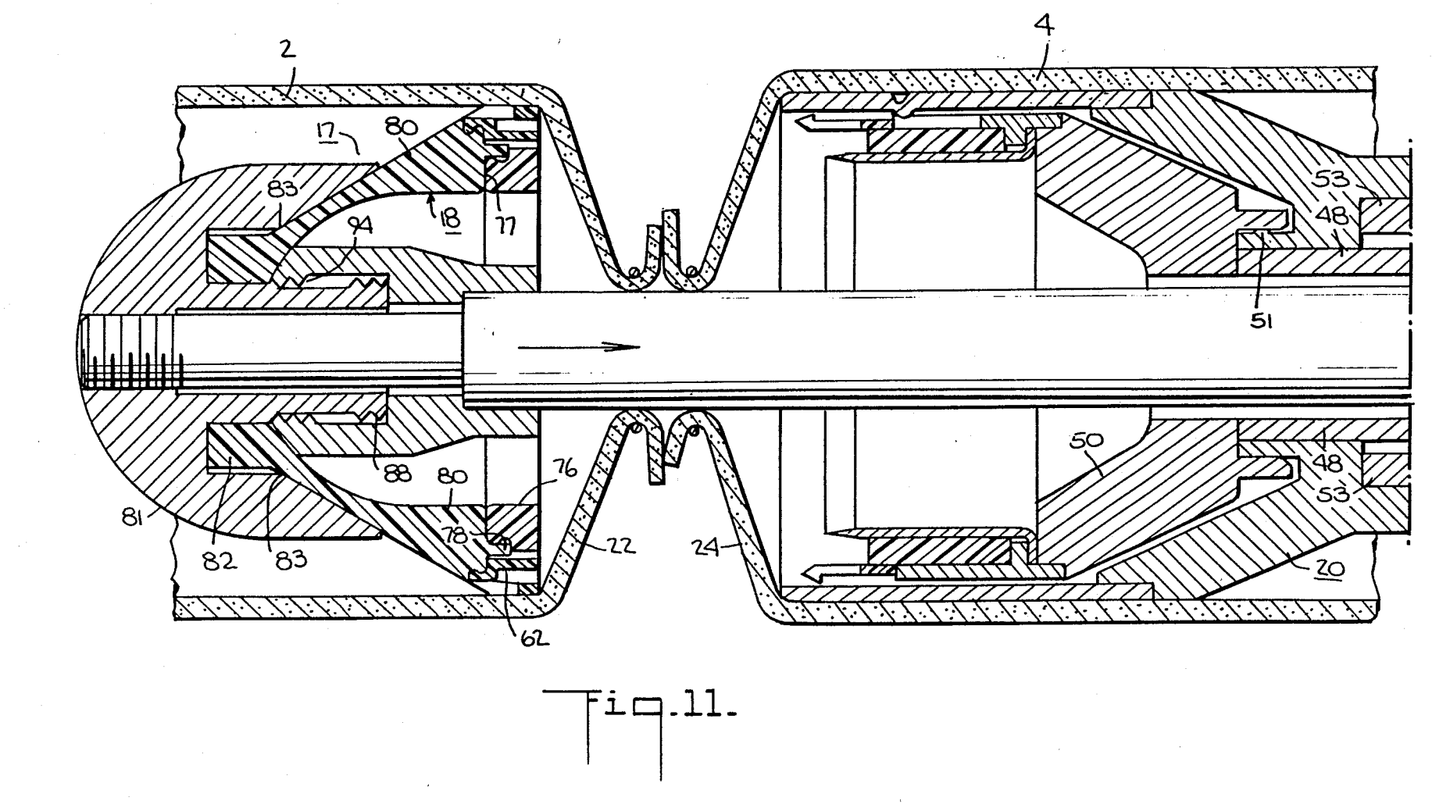
FIG. 11 illustrates a view of the distal end of the surgical stapling apparatus prior to stapling.
Figure 14:
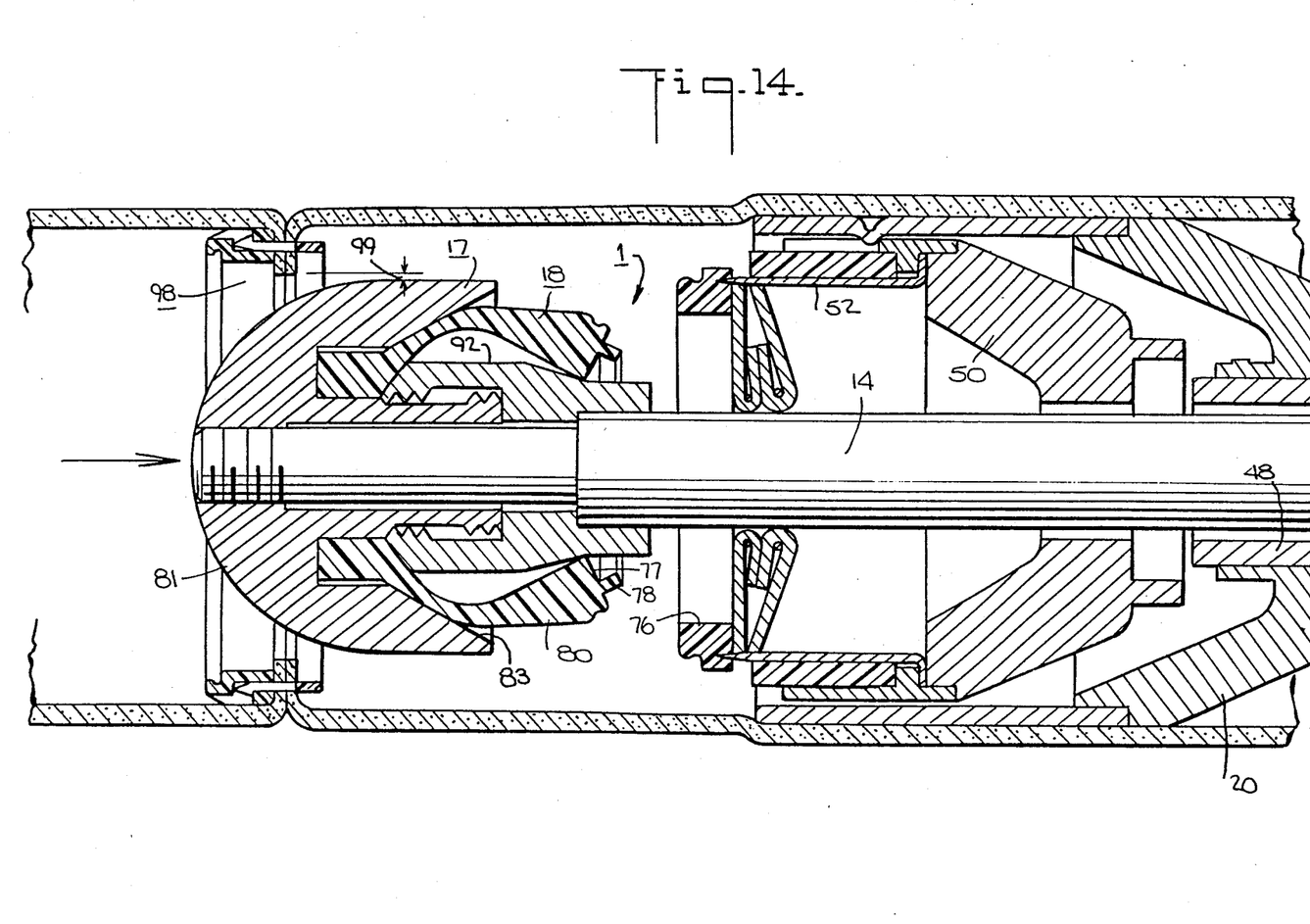
FIG. 14 illustrates a view similar to FIGS. 12 and 13 during withdrawal of the anvil assembly.

Referring to FIGS. 6 and 12, the anvil assembly 17 also includes an anvil head 81 having an internal conical wall (83 as as shown in FIGS. 11 and 14) which receives the anvil with the fingers 80 abutting against the wall. In addition, the anvil head 81 has a central shaft 86 about which the hub 82 is mounted via an axial opening 84. The shaft 86 also has an external screw thread 88 on which a hub retainer 92 is thus via internal screw threads 94. The hub retainer 92 is thus able to freewheel in relation to the anvil head 81, that is, the hub retainer 92 can be threaded into abuttment with the hub 82 with a greater or lesser degree of force. In this way, the anvil head 81 and retainer 92 cooperate to form a means for biasing the fingers 80 of the anvil 18 radially inwardly of the cutting block 76 to permit movement of the fingers 80 radially inwardly in response to removal of the cutting block 76 from the fingers 80. As indicated in FIG. 12, cutting block 76 holds the fingers 80 in a tensioned state. In addition, the fingers 80 are suitably shaped so as to hold the retaining part 62 in a snap fit relation (see FIG. 12). When the cutting block 76 and retaining part 62 are in place, dimensional stability is imparted to the resilient finqers 80.

As indicated in FIG. 12, while the anvil 18 is made of a plastic, the anvil head 81 and retainer ring 92 are made of a metal, such as aluminum. Further, the anvil head 81 is provided with a threaded bore so as to be threaded onto the distal end of the central shaft 14.

Figure 13:
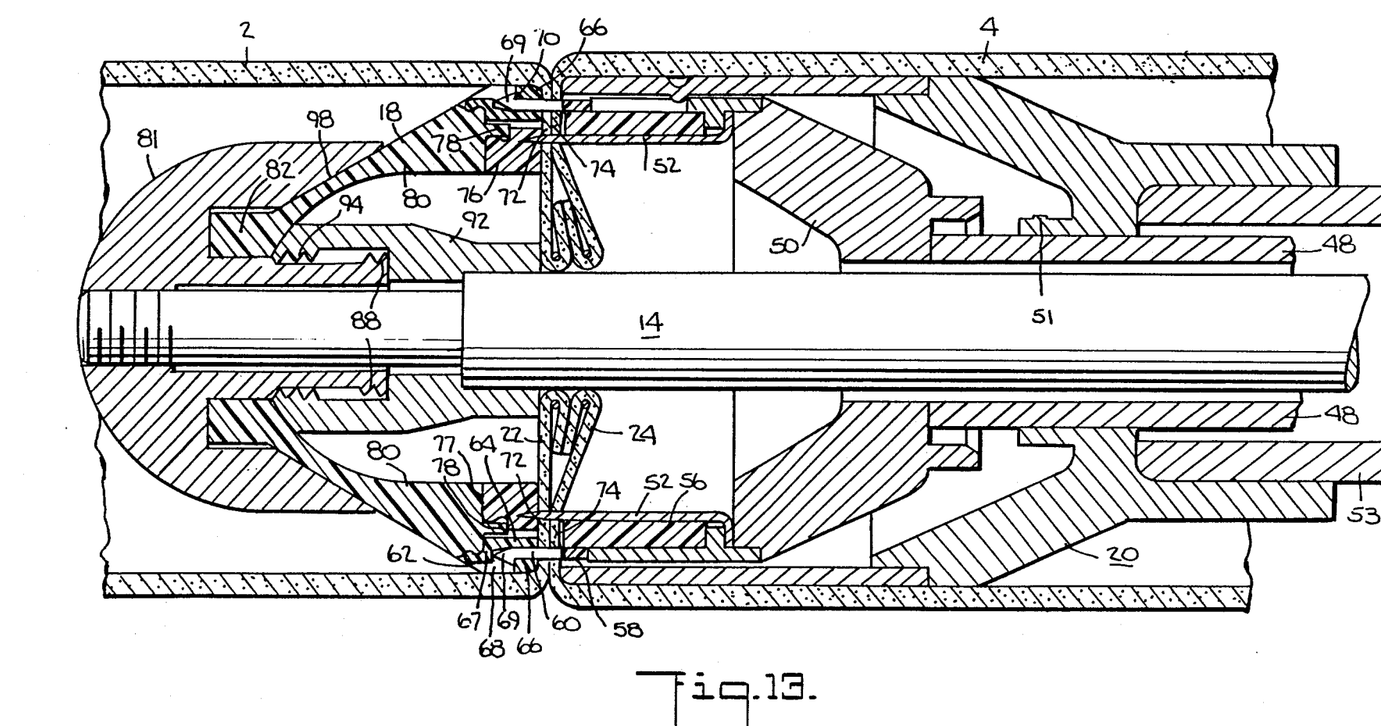
FIG. 13 illustrates a view similar to FIG. 12 of the stapling components after stapling.

Referring to FIG. 11, in use, in order to staple the tubular ends of the tissue together, the stapling apparatus is inserted in a conventional manner. Thereafter, the ends of the tissue 2, 4 are pulled together as indicated in FIG. 11 about the central shaft 14 so as to dispose two areas 22, 24 between the anvil assembly 17 and the fastener holding assembly 20. Thereafter, the shaft 14 is moved proximally via the hand screw 16 so as to move the anvil assembly 17 into a clamped position with the holding assembly 20. In this position, the areas 22, 24 of the tissue 2, 4 are clamped between the anvil 18 and the holding assembly 20. Next, triggering of the instrument via the trigger 28 (see FIG. 1) causes the tube 48 to be moved distally. This in turn moves the actuator 50 distally. As a result, the annular scalpel 52 severs the clamped ends of the tissue on a circular cutting line 99 while penetrating into the cutting block 76. At the same time, the push ring 54 pushes the prong 60 of the stapling part 58 through the clamped ends of the tissue into the annular retaining part 62 with the barb 69 engaging behind the retaining ring 66 as indicated in FIG. 13.

Next, the anvil assembly 17 is moved away from the holding assembly 20 by turning of the handscrew 16 (see FIG. 1). During this time, the annular cutting block 76 which has been imbedded by the annular scalpel 52 remains in place on the scalpel 52 as indicated in FIG. 14. At the same time, the annular stapling part 58 remains engaged in the retaining part 62 so as to staple the tissue ends together in a seam as indicated in FIG. 14. In addition, since the cutting block 76 has been withdrawn from the fingers 80 of the anvil 18, these fingers 80 collapse radially inwardly as also indicated in FIG. 14. The degree of collapse of the fingers 80 is such that the fingers 80 fall inside of the cutting line 99 defined by the seamed tissue. Thus, the stapling apparatus 1 may then be removed from within the stapled-together ends. Of note, when the trigger 38 (see FIG. 4) is released, the compression spring 46 biases the slider 44 to return to a proximal position which, in turn, pulls back the shaft 48 into a position as shown in FIG. 14. The actuator 50 remains within the holding assembly 20, for example, as indicated by means of a detent and a holding ring of the holding assembly 20.

The stapling part 58 and retaining part 62 can be made of any suitable materials, such as nylon, polycarbonate or other material. If a non-permanent fastener is to be used, these parts may be made of a tissue absorbable polymer.

The invention thus provides a surgical fastener of two-part construction which can be readily manipulated and oriented in place for stapling of body tissue in an anastomosis procedure. Because the fastener parts are annular with the prongs of one part fitting into an annular groove of the other part, precise registration of the prongs relative to the annular gap is not required.

The invention also provides a method of fastening together the ends of two tubular body organs which can be carried out in a relative minimum of time and with relatively minimal effort with respect to previously known techniques.

What is claimed is:

1. A surgical fastener comprising
an annular stapling part having a plurality of axially extending circumferentially spaced prongs, each said prong having a sharp tip for piercing tissue;
an annular retaining part having an annular gap for receiving said prongs, said gap being of an axial length less than an axial length of said prongs to permit passage of said prongs therethrough; and
catching means for holding said prongs in said retaining part to clamp the pierced tissue therebetween.

2. A surgical fastener as set forth in claim 1 wherein said catch means includes a radially extending barb on at least some of said prongs for abutting against said retaining part.

3. A surgical fastener as set forth claim 2 wherein each barb is disposed radially of a respective tip.

4. A surgical fastener as set forth in claim 1 wherein said retaining part includes a cylindrical guide wall, a concentrically spaced retaining ring, and means securing said ring to said guide wall in radially spaced relation to define said annular gap to receive said prongs.

5. A surgical fastener as set forth in claim 4 wherein said catch means includes a radially extending barb on each respective prong for abutting said ring on a side remote from said stapling part with said prongs disposed in said gap.

6. A surgical fastener as set forth in claim 5 wherein at least one of said guide wall and ring is radially resiliently deformable to permit passage of said barbs therebetween.

7. A surgical fastener as set forth in claim 1 wherein each said part is made of plastic.

8. A surgical fastener as set forth in claim 1 wherein each of said parts is made of a tissue absorbable polymer.

9. A surgical fastener comprising
an annular stapling part having a plurality of axially extending circumferentially spaced prongs, each said prong having a sharp tip for piercing tissue;
an annular retaining part including an inner cylindrical guide wall and a concentrically disposed outer retaining ring defining an annular gap for receiving said prongs; and
catch means for holding said prongs in said retaining part between said guide wall and said retaining ring.

10. A surgical fastener as set forth in claim 9 wherein said catch means includes a radially extending barb on at least some of said prongs for abutting against said retaining ring.

11. A surgical fastener as set forth in claim 10 wherein at least one of said guide wall and ring is radially resiliently deformable to permit passage of said barbs therebetween.

12. A surgical fastener as set forth in claim 9 wherein each of said parts is made of a tissue absorbable polymer.

* * * * *